United States Patent
Chen et al.

(10) Patent No.: US 11,498,897 B2
(45) Date of Patent: Nov. 15, 2022

(54) METHOD FOR PREPARING LEVETIRACETAM

(71) Applicants: Zhejiang Huahai Pharmaceutical Co., Ltd, Zhejiang (CN); Zhejiang Huahai TianCheng Pharmaceutical Co., Ltd, Zhejiang (CN); Zhejiang Huahai Zhicheng Pharmaceutical Co., Ltd, Zhejiang (CN)

(72) Inventors: Xinlei Chen, Zhejiang (CN); Zhicheng Hu, Zhejiang (CN); Liang Zheng, Zhejiang (CN); Peng Dong, Zhejiang (CN)

(73) Assignees: Zhejiang Huahai Pharmaceutical Co., Ltd., Zhejiang (CN); Zhejiang Huahai Tiancheng Pharmaceutical Co., Ltd., Zhejiang (CN); Zhejiang Huahai Zhicheng Pharmaceutical Co., Ltd., Zhejiang (CN)

( * ) Notice: Subject to any disclaimer, the term of this patent is extended or adjusted under 35 U.S.C. 154(b) by 333 days.

(21) Appl. No.: 16/638,105

(22) PCT Filed: Aug. 9, 2018

(86) PCT No.: PCT/CN2018/099533
§ 371 (c)(1),
(2) Date: Feb. 10, 2020

(87) PCT Pub. No.: WO2019/029598
PCT Pub. Date: Feb. 14, 2019

(65) Prior Publication Data
US 2020/0172479 A1   Jun. 4, 2020

(30) Foreign Application Priority Data

Aug. 10, 2017 (CN) .......................... 201710681337.7

(51) Int. Cl.
*C07D 207/27* (2006.01)
(52) U.S. Cl.
CPC ................ *C07D 207/27* (2013.01)

(58) Field of Classification Search
CPC .................................................. C07D 207/27
USPC ......................................................... 548/551
See application file for complete search history.

(56) References Cited

FOREIGN PATENT DOCUMENTS

| CN | 85105301 A | 1/1987 |
|---|---|---|
| CN | 101270070 A | 9/2008 |
| CN | 101333180 A | 12/2008 |
| CN | 101885696 A | 11/2010 |
| CN | 102863370 A | 1/2013 |
| CN | 106748950 A | 5/2017 |
| CN | 107337628 A | 11/2017 |
| WO | 2006053441 A1 | 5/2006 |

OTHER PUBLICATIONS

English translation of CN107337628A (published on Nov. 10, 2017), translated on Mar. 2, 2022 (Year: 2022).*
Liu et al., "Synthesis of levetiracetam and its derivatives," Chinese Journal of New Drugs, 2007:16(11); 5 pgs.
"Study on the Process Optimization of Levetiracetam," Chinese Master's Theses Full-text Database, Engineering Science and Technology I, ISSN 1674-0246 CN 11-9144/G, 2013; 7 pgs.
Office Action for Chinese Patent Application No. 201710681337.7 dated Apr. 1, 2021; 8 pgs.

* cited by examiner

*Primary Examiner* — Kristin A Vajda
(74) *Attorney, Agent, or Firm* — Umberg Zipser LLP; Jason Tejani

(57) ABSTRACT

A preparing method for high-purity levetiracetam, comprising: adjusting the pH of an extracted aqueous layer obtained by dissociating (S)-α-ethyl-2-oxo-1-pyrrolidineacetic acid (R)-methylbenzylamine salt to 5-9; removing water; adding an organic solvent to form a solution and then performing an esterification reaction with ethyl chloroformate or methylchlorofonmate; and carrying out an ammonolysis reaction to obtain the levetiracetam. The method simplifies production process, increases yield, reduces or even avoids the use of triethylamine in the esterification process, and reduces the emission of a great amount of three wastes.

12 Claims, No Drawings

METHOD FOR PREPARING LEVETIRACETAM

The present application claims the priority of Chinese Patent Application No. 201710681337.7, with the title of "METHOD FOR PREPARING LEVETIRACETAM", filed before the CNIPA on Aug. 10, 2017, which is herein incorporated by reference in its entirety.

FIELD OF THE INVENTION

The invention relates to the field of medicine and chemical industry, in particular to a method for preparing levetiracetam.

BACKGROUND OF THE INVENTION

Levetiracetam with a structural formula below

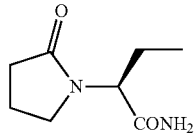

is a second-generation acetylcholine agonist developed by UCB in Belgium and is structurally associated with piracetam. Levetiracetam is a pyrrolidone derivative and is mainly used to treat partial and secondary generalized epilepsy.

In the process of synthesizing levetiracetam, levetiracetam acid, levetiracetam ethyl ester and the like are tended to be produced depending on reaction conditions, and crude levetiracetam with a purity of 98% can be obtained after one refining process subsequently. However, to obtain crude levetiracetam with a purity greater than 99.5%, in the prior art, for example, U.S. Pat. No. 4,696,943 and CN101333180A, (S)-α-ethyl-2-oxo-1-pyrrolidineacetic acid (R)-α-methylbenzylamine salt is treated with an inorganic base and then a first organic solvent is added to extract free (R)-α-methylbenzylamine, and the aqueous layer is collected; then pH of the aqueous layer is adjusted to be strongly acidic to form a precipitate, and then after filtering, washing, drying, recrystallization and other steps, (S)-α-ethyl-2-oxo-1-pyrrolidineacetic acid is obtained; then esterification and ammonolysis are performed to obtain levetiracetam. Although this process can improve the purity of the levetiracetam crude, it is complicated with a low yield and a large amount of triethylamine needs to be used in the esterification process, which not only results in a large amount of three wastes, but also has a high cost. The structure of (S)-α-ethyl-2-oxo-1-pyrrolidineacetic acid (R)-α-methylbenzylamine salt is shown below:

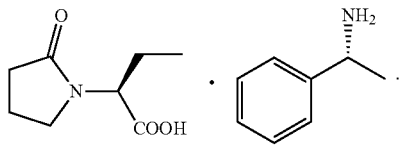

SUMMARY OF THE INVENTION

The invention provides a method for preparing levetiracetam in a high purity comprising 1) mixing (S)-α-ethyl-2-oxo-1-pyrrolidineacetic acid (R)-α-methylbenzylamine salt with an aqueous solution of inorganic base, adding a first organic solvent to extract free (R)-α-methylbenzylamine, and collecting an aqueous layer;

2) adding an acid to adjust the aqueous layer obtained in step 1) to pH 5-9; then removing water to obtain an oil, and then dissolving the oil with a second organic solvent to obtain a solution containing (S)-α-ethyl-2-oxo-1-pyrrolidineacetic acid; preferably, the acid is one of hydrochloric acid and sulfuric acid, or a combination thereof;

3) performing an esterification reaction of (S)-α-ethyl-2-oxo-1-pyrrolidineacetic acid in the solution obtained in step 2), and then carrying out an ammonolysis reaction to obtain levetiracetam.

It should be noted that (S)-α-ethyl-2-oxo-1-pyrrolidineacetic acid (R)-α-methylbenzylamine salt used in the present invention can be prepared by a method in the prior art which is not limited herein.

In some embodiments of the present invention, the esterification reaction of (S)-α-ethyl-2-oxo-1-pyrrolidineacetic acid in the solution is performed with ethyl chloroformate or methyl chloroformate. Preferably, the esterification reaction can be performed in the absence of triethylamine, and levetiracetam with higher yield and purity can be obtained.

In some embodiments of the present invention, the esterified product is contacted with ammonia to perform an ammonolysis reaction. The ammonia may be derived from such as liquid ammonia, ammonia gas, or an organic solution of ammonia gas.

In some embodiments of the present invention, in step 1), (S)-α-ethyl-2-oxo-1-pyrrolidineacetic acid (R)-α-methylbenzylamine salt is mixed with the aqueous solution of inorganic base, then further stirred to accelerate the dissociation of (R)-α-methylbenzylamine. In an embodiment, it may be stirred for 10-60 minutes.

In some embodiments of the present invention, the first organic solvent may be added once or more in step 1) to extract free (R)-α-methylbenzylamine.

In some embodiments of the present invention, the inorganic base in step 1) is one selected from the group consisting of sodium hydroxide, potassium hydroxide, and lithium hydroxide, or a combination of at least two of them. In an embodiment, when the inorganic base includes sodium hydroxide, the sodium hydroxide can be derived from a solution of 30% by weight of sodium hydroxide, which is commonly used in the industry.

The molar ratio of the inorganic base and (S)-α-ethyl-2-oxo-1-pyrrolidineacetic acid (R)-α-methylbenzylamine salt used in step 1) is 1:1 to 1.4:1, preferably 1.1:1 to 1.2:1.

In some embodiments of the present invention, the equivalent of the inorganic base in step 1) is 1.0-1.6, preferably 1.1-1.3.

In some embodiments of the present invention, the first organic solvent in step 1) is one selected from the group consisting of benzene, xylene, toluene, n-butyl acetate, n-hexane, n-heptane, cyclohexane and the like, or a combination of at least two of them, preferably toluene.

In some embodiments of the present invention, in step 2), it is preferable to adjust the aqueous layer to pH 6-8, and more preferably to pH 7-8.

In some embodiments of the present invention, removing water in step 2) may be performed by direct distillation to remove water, and preferably, by azeotropic dehydration via adding a third organic solvent capable of azeotroping with water. The third organic solvent is one selected from the group consisting of benzene, xylene, toluene, n-propanol, isopropanol, n-butanol, and isobutanol, or a combination of at least two of them, and more preferably toluene.

In some embodiments of the present invention, in the solution obtained after dissolving with the second organic solvent in step 2), water content is required to be ≤1% by weight, preferably less than 0.5% by weight, based on the total weight of the solution.

In some embodiments of the present invention, the second organic solvent is one selected from the group consisting of dichloromethane, chloroform, carbon tetrachloride, and 1,2-dichloroethane, or a combination of at least two of them, preferably dichloromethane.

In some embodiments of the present invention, after the completion of the ammonolysis reaction in step 3), it is preferred to use filtration to remove the inorganic salts produced during the esterification and the ammonolysis processes, and then remove the organic solvent by distillation, and further recrystallize to obtain levetiracetam.

In some embodiments of the present invention, high purity refers to a purity of 95% or more, preferably 98% or more, more preferably 99% or more, and most preferably 99.8% or more.

In the process of synthesizing levetiracetam according to the present invention, (S)-α-ethyl-2-oxo-1-pyrrolidineacetic acid (R)-α-methylbenzylamine salt is mixed with an aqueous solution of inorganic base, and then a first organic solvent is added to extract free (R)-α-methylbenzylamine, and the collected aqueous layer is adjusted to pH 5-9; after obtaining the solution containing (S)-α-ethyl-2-oxo-1-pyrrolidineacetic acid, esterification reaction and ammonolysis reaction can be directly performed. Compared to the process in the prior art, this method simplifies production process, improves yield, while greatly reduces or even avoids the use of triethylamine in the esterification process, and reduces the emissions of a large number of three wastes.

DETAILED DESCRIPTION OF THE INVENTION

In order to make the objectives, technical solutions, and advantages of the present invention clearer, the present invention is further described in detail through specific examples. It is obviously that the described examples are only a part of the examples of the present invention, but not all the examples. Based on the examples of the present invention, all other examples obtained by a person of ordinary skill in the art without creative efforts shall fall within the protection scope of the present invention.

Example 1

130 g of (S)-α-ethyl-2-oxo-1-pyrrolidineacetic acid (R)-α-methylbenzylamine salt, 100 g of water, 50 ml of solution of 30% by weight of sodium hydroxide were mixed and stirred for 30 minutes; free (R)-α-methylbenzylamine was repeatedly extracted with 3×100 ml of toluene. The aqueous layer was collected and acidified with hydrochloric acid to pH=7, and added with 100 ml of toluene. The water was removed under reduced pressure at ≤60° C. to obtain an oil, then to which added 300 ml of dichloromethane to dissolve the oil and to obtain a dichloromethane solution containing (S)-α-ethyl-2-oxo-1-pyrrolidineacetic acid; and the measured water content was 0.54% by weight.

51 g of ethyl chloroformate was added dropwise to the dichloromethane solution described above, to perform an esterification reaction at −10° C. for 2 hours. 200 ml of a solution of 13.5% by weight of ammonia gas in dichloromethane was added to perform an ammonolysis reaction at −15 to −10° C. for 2 hours. The inorganic salt was removed by filtration, and the solvent was distilled off. 300 ml of acetone was added for recrystallization, and the obtained mixture was filtrated. The filter cake was rinsed with acetone to obtain levetiracetam with a yield of 81% (a purity of 99.9%, determined by high performance liquid chromatography).

Example 2

130 g of (S)-α-ethyl-2-oxo-1-pyrrolidineacetic acid (R)-α-methylbenzylamine salt, 100 g of water, 50 ml of solution of 30% by weight of sodium hydroxide were mixed and stirred for 30 minutes; free (R)-α-methylbenzylamine was repeatedly extracted with 3×100 ml of toluene. The aqueous layer was collected and acidified with hydrochloric acid to pH=6, and added with 100 ml of toluene. The water was removed under reduced pressure at ≤60° C. to obtain an oil, then to which added 300 ml of dichloromethane to dissolve the oil and to obtain a dichloromethane solution containing (S)-α-ethyl-2-oxo-1-pyrrolidineacetic acid; and the measured water content was 0.3% by weight.

51 g of ethyl chloroformate was added dropwise to the dichloromethane solution described above, to perform an esterification reaction at −10° C. for 2 hours. 200 ml of a solution of 13.5% by weight of ammonia gas in dichloromethane was added to perform an ammonolysis reaction at −15 to −10° C. for 2 hours. The inorganic salt was removed by filtration, and the solvent was distilled off. 300 ml of acetone was added for recrystallization, and the obtained mixture was filtrated. The filter cake was rinsed with acetone to obtain levetiracetam with a yield of 83% (a purity of 99.9%, determined by high performance liquid chromatography).

Example 3

130 g of (S)-α-ethyl-2-oxo-1-pyrrolidineacetic acid (R)-α-methylbenzylamine salt, 100 g of water, 50 ml of solution of 30% by weight of sodium hydroxide solution were mixed and stirred for 30 minutes; free (R)-α-methylbenzylamine was repeatedly extracted with 3×100 ml of toluene. The aqueous layer was collected and the aqueous layer was acidified with hydrochloric acid to pH=6, and added with 100 ml of toluene. The water was removed under reduced pressure at ≤60° C. to obtain an oil, then to which added 300 ml of dichloromethane to dissolve the oil and to obtain a dichloromethane solution containing (S)-α-ethyl-2-oxo-1-pyrrolidineacetic acid; and the measured water content was 0.92% by weight.

51 g of ethyl chloroformate was added dropwise to the dichloromethane solution described above, to perform an esterification reaction at −10° C. for 2 hours. 200 ml of a solution of 13.5% by weight of ammonia gas in dichloromethane was added to perform an ammonolysis reaction at −15 to −10° C. for 2 hours. The inorganic salt was removed by filtration, and the solvent was distilled off. 300 ml of acetone was added for recrystallization, and the obtained mixture was filtrated. The filter cake was rinsed with acetone to obtain levetiracetam with a yield of 75% (a purity of 99.9%, determined by high performance liquid chromatography).

Example 4

130 g of (S)-α-ethyl-2-oxo-1-pyrrolidineacetic acid (R)-α-methylbenzylamine salt, 100 g of water, 50 ml of solution of 30% by weight of sodium hydroxide were mixed and stirred for 30 minutes; free (R)-α-methylbenzylamine was repeatedly extracted with 3×100 ml of toluene. The aqueous layer was collected and acidified with hydrochloric acid to pH=9, and added with 100 ml of toluene. The water was removed under reduced pressure at ≤60° C. to obtain an oil, then to which added 300 ml of dichloromethane to dissolve the oil and to obtain a dichloromethane solution containing (S)-α-ethyl-2-oxo-1-pyrrolidineacetic acid; and the measured water content was 0.41% by weight.

51 g of ethyl chloroformate was added dropwise to the dichloromethane solution described above, and to perform an esterification reaction at −10° C. for 2 hours. 200 ml of a solution of 13.5% by weight of ammonia gas in dichloromethane was added to perform an ammonolysis reaction at −15 to −10° C. for 2 hours. The inorganic salt was removed by filtration, and the solvent was distilled off 300 ml of acetone was added for recrystallization, and the obtained mixture was filtrated. The filter cake was rinsed with acetone to obtain levetiracetam with a yield of 79% (a purity of 99.8%, determined by high performance liquid chromatography).

Example 5

130 g of (S)-α-ethyl-2-oxo-1-pyrrolidineacetic acid (R)-α-methylbenzylamine salt, 100 g of water, 50 ml of solution of 30% by weight of sodium hydroxide were mixed and stirred for 30 minutes; free (R)-α-methylbenzylamine was repeatedly extracted with 3×100 ml of toluene. The aqueous layer was collected and acidified with hydrochloric acid to pH=8, and added with 100 ml of toluene. The water was removed under reduced pressure at ≤60° C. to obtain an oil, then to which added 300 ml of dichloromethane to dissolve the oil and to obtain a dichloromethane solution containing (S)-α-ethyl-2-oxo-1-pyrrolidineacetic acid; and the measured water content was 0.2% by weight.

51 g of ethyl chloroformate was added dropwise to the dichloromethane solution described above to perform an esterification reaction at −10° C. for 2 hours. 200 ml of a solution of 13.5% by weight of ammonia gas in dichloromethane was added to perform an ammonolysis reaction at −15 to −10° C. for 2 hours. The inorganic salt was removed by filtration, and the solvent was distilled off 300 ml of acetone was added for recrystallization, and the obtained mixture was filtrated. The filter cake was rinsed with acetone to obtain levetiracetam with a yield of 78% (a purity of 99.8%, determined by high performance liquid chromatography).

Example 6

130 g of (S)-α-ethyl-2-oxo-1-pyrrolidineacetic acid (R)-α-methylbenzylamine salt, 100 g of water, 50 ml of solution of 30% by weight of sodium hydroxide were mixed and stirred for 30 minutes; free (R)-α-methylbenzylamine was repeatedly extracted with 3×100 ml of toluene. The aqueous layer was collected and acidified with hydrochloric acid to pH=7, and added with 100 ml of toluene. The water was removed under reduced pressure at ≤60° C. to obtain an oil, then to which added 300 ml of dichloromethane to dissolve the oil and to obtain a dichloromethane solution containing (S)-α-ethyl-2-oxo-1-pyrrolidineacetic acid; the measured water content was 0.19% by weight.

51 g of ethyl chloroformate was added dropwise to the dichloromethane solution described above to perform an esterification reaction at −10° C. for 2 hours. 200 ml of a solution of 13.5% by weight of ammonia gas in dichloromethane was added to perform an ammonolysis reaction at −15 to −10° C. for 2 hours. The inorganic salt was removed by filtration, and the solvent was distilled off 300 ml of acetone was added for recrystallization, and the obtained mixture was filtrated. The filter cake was rinsed with acetone to obtain levetiracetam with a yield of 85% (a purity of 99.8%, determined by high performance liquid chromatography).

Example 7

130 g of (S)-α-ethyl-2-oxo-1-pyrrolidineacetic acid (R)-α-methylbenzylamine salt, 100 g of water, 50 ml of solution of 30% by weight of sodium hydroxide solution were mixed and stirred for 30 minutes; free (R)-α-methylbenzylamine was repeatedly extracted with 3×100 ml of toluene. The aqueous layer was collected and acidified with hydrochloric acid to pH=7, and added with 100 ml of toluene. The water was removed under reduced pressure at ≤60° C. to obtain an oil, then to which added 300 ml of dichloromethane to dissolve the oil and to obtain a dichloromethane solution containing (S)-α-ethyl-2-oxo-1-pyrrolidineacetic acid; and the measured water content was 0.35% by weight. 2.2 g of triethylamine was added to the dichloromethane solution and dissolved.

51 g of ethyl chloroformate was added dropwise to the dichloromethane solution in which triethylamine was dissolved described above, to perform an esterification reaction at −10° C. for 2 hours. 200 ml of a solution of 13.5% by weight of ammonia gas in dichloromethane was added, to perform an ammonolysis reaction at −15 to −10° C. for 2 hours. The inorganic salt was removed by filtration, and the solvent was distilled off 300 ml of acetone was added for recrystallization, and the obtained mixture was filtrated. The filter cake was rinsed with acetone to obtain levetiracetam with a yield of 82% (a purity of 99.8%, determined by high performance liquid chromatography).

Example 8

130 g of (S)-α-ethyl-2-oxo-1-pyrrolidineacetic acid (R)-α-methylbenzylamine salt, 100 g of water, 50 ml of solution of 30% by weight of sodium hydroxide were mixed and stirred for 30 minutes; free (R)-α-methylbenzylamine was repeatedly extracted with 3×100 ml of toluene. The aqueous layer was collected and acidified with hydrochloric acid to pH=7, and added with 100 ml of toluene. The water was removed under reduced pressure at ≤60° C. to obtain an oil, then to which added 300 ml of dichloromethane to dissolve the oil and to obtain a dichloromethane solution containing (S)-α-ethyl-2-oxo-1-pyrrolidineacetic acid; and the measured water content was 0.4% by weight. 4.4 g of triethylamine was added to the dichloromethane solution and dissolved.

51 g of ethyl chloroformate was added dropwise to the dichloromethane solution in which triethylamine was dissolved described above, to perform an esterification reaction at −10° C. for 2 hours. 200 ml of a solution of 13.5% by weight ammonia gas in dichloromethane was added, and an ammonolysis reaction was performed at −15 to −10° C. for 2 hours. The inorganic salt was removed by filtration, and the solvent was distilled off 300 ml of acetone was added for recrystallization, and the obtained mixture was filtrated. The filter cake was rinsed with acetone to obtain levetiracetam with a yield of 80% (a purity of 99.9%, determined by high performance liquid chromatography).

Example 9

130 g of (S)-α-ethyl-2-oxo-1-pyrrolidineacetic acid (R)-α-methylbenzylamine salt, 100 g of water, 50 ml of solution of 30% by weight of sodium hydroxide solution were mixed and stirred for 30 minutes; free (R)-α-methylbenzylamine was repeatedly extracted with 3×100 ml of toluene. The aqueous layer was collected and acidified with hydrochloric acid to pH=7, and added with 100 ml of toluene. The water was removed under reduced pressure at ≤60° C. to obtain an oil, then to which added 300 ml of dichloromethane to dissolve the oil and to obtain a dichloromethane solution containing (S)-α-ethyl-2-oxo-1-pyrrolidineacetic acid; and the measured water content was 0.4% by weight. 11 g of triethylamine was added to the dichloromethane solution and dissolved.

51 g of ethyl chloroformate was added dropwise to the dichloromethane solution in which triethylamine was dissolved described above, to perform an esterification reaction at −10° C. for 2 hours. 200 ml of a solution of 13.5% by weight of ammonia gas in dichloromethane was added to perform an ammonolysis reaction at −15 to −10° C. for 2 hours. The inorganic salt was removed by filtration, and the solvent was distilled off 300 ml of acetone was added for recrystallization, and the obtained mixture was filtrated. The filter cake was rinsed with acetone to obtain levetiracetam with a yield of 84% (a purity of 99.8%, determined by high performance liquid chromatography).

Examples 10-13

Levetiracetam in Examples 10 to 13 was prepared according to the method described in Example 1, except that the first organic solvent, the second organic solvent, and the third organic solvent shown in Table 1 were used to replace the corresponding organic solvents in Example 1 in equal amounts, respectively.

TABLE 1

|  | First organic solvent | Second organic solvent | Third organic solvent |
| --- | --- | --- | --- |
| Example 10 | xylene | chloroform | xylene |
| Example 11 | n-butyl acetate | carbon tetrachloride | n-propanol |
| Example 12 | n-hexane | 1,2-dichloroethane | n-butanol |
| Example 13 | cyclohexane | dichloromethane/chloroform (v:v = 1:1) | benzene |

Testing results show that the methods of Examples 10-13 can also obtain levetiracetam with higher yield and purity.

The above are only preferred examples of the present invention, and are not intended to limit the present invention. Any modifications, equivalents, improvements, etc., which are made within the spirit and principles of the present invention, should be included within the scope of the present invention.

The invention claimed is:

1. A method for preparing levetiracetam in a high purity comprising
   1) mixing (S)-α-ethyl-2-oxo-1-pyrrolidineacetic acid (R)-α-methylbenzylamine salt with an aqueous solution of inorganic base, adding a first organic solvent to extract free (R)-α-methylbenzylamine, and collecting an aqueous layer;
   2) adding an acid to adjust the aqueous layer obtained in step 1) to pH 5-9; then removing water to obtain an oil; then dissolving the oil with a second organic solvent to obtain a solution containing (S)-α-ethyl-2-oxo-1-pyrrolidineacetic acid;
   3) performing an esterification reaction of (S)-α-ethyl-2-oxo-1-pyrrolidineacetic acid in the solution obtained in step 2), with ethyl chloroformate or methyl chloroformate, and then an ammonolysis reaction to obtain levetiracetam,
   wherein the acid is hydrochloric acid.

2. The method according to claim 1, wherein the inorganic base in step 1) is one selected from the group consisting of sodium hydroxide, potassium hydroxide, and lithium hydroxide.

3. The method according to claim 1, wherein the molar ratio of the inorganic base and (S)-α-ethyl-2-oxo-1-pyrrolidineacetic acid (R)-methylbenzylamine salt used in step 1) is 1:1- 1.6:1.

4. The method according to claim 1, wherein the pH in step 2) is adjusted to 6-8.

5. The method according to claim 4, wherein the pH in step 2) is adjusted to 7-8.

6. The method according to claim 1, wherein removing water in step 2) is performed by adding a third organic solvent capable of azeotroping with water for azeotropic dehydration.

7. The method according to claim 6, wherein the third organic solvent is toluene.

8. The method according to claim 1, wherein in the solution obtained in step 2), a water content is required to be ≤1% by weight, based on the total weight of the solution.

9. The method according to claim 3, wherein the molar ratio of the inorganic base and (S)-α-ethyl-2-oxo-1-pyrrolidineacetic acid (R)-methylbenzylamine salt used in step 1) is 1.1:1-1.3:1.

10. The method according to claim 1, wherein the first organic solvent in step 1) is toluene.

11. The method according to claim 8, wherein in the solution obtained in step 2), the water content is required to be less than 0.5% by weight, based on the total weight of the solution.

12. The method according to claim 1, wherein the second organic solvent in step 2) is dichloromethane.

* * * * *